United States Patent [19]

Ahluwalia et al.

[11] Patent Number: 5,554,608
[45] Date of Patent: Sep. 10, 1996

[54] INHIBITION OF HAIR GROWTH

[76] Inventors: Gurpreet S. Ahluwalia, 8632 Stable View Ct., Gaithersburg, Md. 20879; Douglas Shander, 16112 Howard Landing Dr., Gaithersburg, Md. 20878; Peter Styczynski, 3709 Roop Rd., New Windsor, Md. 21776

[21] Appl. No.: 314,327

[22] Filed: Sep. 28, 1994

[51] Int. Cl.$^6$ ............... A61K 31/55; A61K 31/54; A61K 31/505; A61K 31/47
[52] U.S. Cl. ............... 514/212; 514/217; 514/225.5; 514/258; 514/313; 514/400; 514/459; 514/523; 514/679
[58] Field of Search ............... 514/212, 217, 514/225.5, 258, 313, 400, 459, 523, 679

[56] References Cited

U.S. PATENT DOCUMENTS

| | | | |
|---|---|---|---|
| 3,426,137 | 2/1969 | Philpitt et al. | 424/330 |
| 4,039,669 | 8/1977 | Beyler et al. | 424/243 |

(List continued on next page.)

FOREIGN PATENT DOCUMENTS

| | | |
|---|---|---|
| 0470490 | 2/1992 | European Pat. Off. . |
| 0532219A2 | 3/1993 | European Pat. Off. . |
| 0648488 | 4/1995 | European Pat. Off. . |
| 2709952 | 3/1995 | France . |
| 62298513 | 12/1987 | Japan . |
| 01238515 | 9/1989 | Japan . |
| 02273610 | 11/1990 | Japan . |
| 04182415 | 6/1992 | Japan . |
| 1458349 | 12/1976 | United Kingdom . |

OTHER PUBLICATIONS

Abstract, *Journal of Investigative Dermatology*, vol. 104, No. 4, p. 606 (Apr. 1995).
Powis et al., "Doxorubicin–induced hair loss in the Angora rabbit . . . ", *Cancer Chemoter. Pharmacol.*, vol. 20, No. 4, pp. 291–296 (1987).
Rodriguez et al., "Minoxidil (Mx) as a prophylaxis of doxorubicin–induced alopecia", *Annals of Oncology*, vol. 5, No. 8, pp. 769–770 (1994).
Dumont et al., "Inhibition of Experimental Metastasis and Cell Adhesion of B16F1 Melanoma Cells by Inhibitors of Protein Kinase C", *Cancer Research*, 52:1195–1200 (Mar. 1, 1992).
Casnellie, "Protein Kinase Inhibitors: Probes for the Functions of Protein Phosphorylation", *Advances in Pharmacology*, 22:167–205 (1991).
Hidaka et al., "Pharmacology of Protein Kinase Inhibitors", *Annu. Rev. Pharmacol. Toxicol.*, 32:377–97 (1992).
Powis, "Signalling targets for anticancer drug development", *TiPS*, 12:188–194 (May, 1991).
Kinnel et al., "11–Hydroxystaurosporine: A Highly Cytotoxic, Powerful Protein Kinase C Inhibitor from a Tunicate", *J. Org. Chem.*, 57:6327–6329 (1992).
Loomis et al., "Sangivamyein, a Nucleoside Analogue, Is a Potent Inhibitor of Protein Kinase C", *Journal of Biological Chemistry*, 263:1682–1692 (Feb., 1988).

Schweizer et al., "Induction of the Formation of New Hair Follicles in Mouse Tail Epidermis by the Tumor Promoter 12–O– Tetradecanoylphorbol–13–acetate", *Cancer Research*, 37:4195–4201 (Nov. 1977).
Inohara et al., "Effects of protein kinase C activators on mouse skin in vivo", *Arch. Dermatol. Res.*, 280:182–184 (1988).
Bollag et al., "Effects of the Selective Protein Kinase C Inhibitor, Ro 31–7549, on the Proliferation of Cultured Mouse Epidermal Keratinocytes", *Journal of Investigative Dermatology*, 100:240–246 (Mar. 1993).
Mori et al., "Inhibitory Action of Chlorpromazine, Dibucaine, and Other Phospholipid–interacting Drugs on Calcium–activated, Phospholipid–dependent Protein Kinase", *Journal of Biological Chem.*, 255:8378–8380 (1980).
O'Brian et al., "Inhibition of protein kinase C by the 12–O–tetradecanoylphorbol–13–acetate antagonist glycyrrhetic", *Cancer Letters*, 49:9–12 (1990).
Reddy et al., "Curcumin is a non–competitive and selective inhibitor of phosphorylase kinase", *FEBS Letters*, 341:19–22 (1994).
Kulanthaivel et al., "Balanol: A Novel and Potent Inhibitor of Protein Kinase C from the Fungus *Verticillium balanoides*" *J. Am. Chem. Soc.*, 115:6452–6453 (1993).
Hannun et al., "Lysosphingolipids Inhibit Protein Kinase C: Implications for the Sphingolipidoses", *Science*, 235:670–674 (Feb., 1987).
Kleinschroth et al., "Non–Glycosidic/Non–Aminoalkyl––Substituted Indolocarbazoles as Inhibitors of Protein Kinase C", *Bioorganic & Medicinal Chemistry Letters*, 3:1959–1964 (1993).
Hegemann et al., "Anti–proliferative effects of protein kinase C inhibitors in human keratinocytes", *Journal of Dermatological Science*, 4:18–25 (1992).
Petros et al., "Substituted 2–(Aminomethyl)piperidines: A Novel Class of Selective Protein Kinase C Inhibitors", *J. Med. Chem.*, 34:2928–2931 (1991).
Wilkinson et al., "Isoenzyme specificity of bisindolylmaleimides, selective inhibitors of protein kinase C", *Biochem. J.*, 294:335–337 (1993).
Harmon et al., "12–O–Tetradecanoylphorbol–13–Acetate Inhibits Human Hair Follicle Growth and Hair Fiber Production in Whole–Organ Cultures", *SID Abstracts*, 102:533 (Apr., 1994).
Simpson et al., "The effect of topically applied progesterone on sebum excretion rate", *British Journal of Dermatology*, 100:687–692 (1979).
Messenger, "The Control of Hair Growth: An Overview", *Journal of Investigative Dermatology*, 101:4s–9s (Jul., 1993).
Sato, "The Hair Cycle and its Control Mechanism", *Biology and Disease of the Hair*, 3–13 (1975).
Shander et al., "Reduction of Hair Growth", patent application filed Dec. 22, 1992, Ser. No. 07/995,037 (allowed Oct. 18, 1994).
CA 108: 106051, Powis et al., 1987.

*Primary Examiner*—Kimberly Jordan
*Attorney, Agent, or Firm*—Fish & Richardson P.C.

[57] ABSTRACT

Mammalian hair growth is reduced by applying to the skin a composition including an inhibitor of protein kinase C.

33 Claims, No Drawings

U.S. PATENT DOCUMENTS

| | | | |
|---|---|---|---|
| 4,139,638 | 2/1979 | Neri et al. | 424/324 |
| 4,161,540 | 7/1979 | Neri et al. | 424/324 |
| 4,191,775 | 3/1980 | Glen | 424/304 |
| 4,269,831 | 5/1981 | Ferrari et al. | 424/241 |
| 4,370,315 | 1/1983 | Greff et al. | 424/94 |
| 4,720,489 | 1/1988 | Shander | 514/171 |
| 4,885,289 | 12/1989 | Breuer et al. | 514/170 |
| 5,095,007 | 3/1992 | Ahluwalia | 514/23 |
| 5,096,911 | 3/1992 | Ahluwalia et al. | 514/380 |
| 5,132,293 | 7/1992 | Shander et al. | 514/46 |
| 5,143,925 | 9/1992 | Shander et al. | 514/378 |
| 5,189,212 | 2/1993 | Ruenitz | 562/468 |
| 5,271,942 | 12/1993 | Heverhagen | 424/451 |
| 5,300,284 | 4/1994 | Wiechers et al. | 424/70 |
| 5,364,885 | 11/1994 | Ahluwalia et al. | 514/563 |

INHIBITION OF HAIR GROWTH

The invention relates to a method of reducing unwanted hair growth in mammals.

A main function of mammalian hair is to provide environmental protection. However, that function has largely been lost in humans, in whom hair is kept or removed from various parts of the body essentially for cosmetic reasons. For example, it is generality preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts and can also promote the perception of an increase in the rate of hair regrowth. Shaving also can leave stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

It has now been found that unwanted mammalian (including human) hair growth—particularly androgen-stimulated hair growth—can be inhibited by applying to the skin a composition including a protein kinase C ("PKC") inhibitor in an amount effective to reduce hair growth. The unwanted hair growth which is reduced may be normal hair growth, or hair growth that results from an abnormal or diseased condition.

PKC is a phospholipid-dependent, calcium-sensitive family of enzymes that have the ability to phosphorylate proteins. PKC includes an ATP binding cite, a calcium binding site, and a region which interacts with phospholipid. Preferred inhibitors of PKC include those inhibitors that interact with one or more of these specific binding sites.

Among the inhibitors of PKC that can be used are (1) isoquinoline sulfonamides such as 1-(5-isoquinolinyl sulfonyl)-2-methylpiperizine and its derivatives (J. Biol. Chem. 264:810–815, 1989); (2) bisindolylmaleimides such as 3-[1-(3-dimethylamino)propyl]-1H-indol-3-yl]-4-(1H-indol-3-yl)-1H-pyyrole-2,5-dione monohydrochloride (GF109203X), Ro 31-7549, and derivatives of Ro 31-7549 (Biochem. J. 294:335–337, 1993; J. Biol. Chem. 266:15771–15781, 1991; and J. Invest. Dermatol. 100:240–246, 1993); (3) phenothiazine derivatives such as thioridazine, trifluoperizine, and triflucarbine (J. Dermat. Sci. 4:18–25, 1992; and J. Biol. Chem. 255:8378–8380, 1980); (4) lysosphingolipids such as sphingosine and derivatives of sphingosine (Science 235:670–674, 1987; and Ann. Rev. Pharmacol. Toxicol. 32:377–397, 1992); (5) staurosporine, and derivatives of staurosporine such as 7-oxostaurosporine and 11-hydroxystaurosporine (Carcinogenesis 13:355–359, 1992; J. Antibiot. 45:195–198, 1992; and J. Org. Chem. 57:6327–6329, 1992); (6) verapamil, phentolamine and imipramine (J. Biol. Chem. 255:8378–8380, 1980); (7) L-ascorbic acid 6-palmitate (Cancer Res. 47:6633–6638, 1987); (8) glycyrrhetinic acid glycoside and 18β-glycyrrhetinic acid (Cancer Letters 49:9–12, 1990); (9) polymyxin B, sangivamycin, and doxorubicin-Fe(III) (J. Dermat. Sci. 4:18–25, 1992; J. Biol. Chem. 263:1682–1692, 1988; and Trends in Pharmacol. Sci. 12:188–194, 1991); (10) the fungal product, balanol, isolated from *Verticillium balanoides* (J. Am. Chem. Soc. 115:6452–6453, 1993); (11) substituted indolocarbazoles (Bioorg. Med. Chem. Let. 3:1959–1964, 1993); (12) 2-(aminomethyl)piperidines (J. Med. Chem. 34:2928–2931, 1991); (13) curcumin (FEBS Letters 341:19–22, 1994); (14) 4-propyl-5(4-pyridinyl)-2-(3H)-oxazolone (Cancer Research 52:1195–1200, 1992); and (15) dequalinium (Trends in Pharmacol. Sci. 12:188–194, 1991). The inhibitors can be irreversible or reversible (competitive and non-competitive).

The inhibitor of PKC preferably is incorporated in a topical composition which includes a non-toxic dermatologically acceptable vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US 93/0506A. In addition, a penetration enhancer may be added to the vehicle to further enhance the effectiveness of the formulation.

The concentration of the inhibitor in the composition may be varied over a wide range up to a saturated solution, preferably from 0.1% to 30% by weight or even more; the reduction of hair growth increases as the mount of inhibitor applied increases per unit area of skin. The maximum amount effectively applied is limited only by the rate at which the inhibitor penetrates the skin. Generally, the effective amounts range from 100 to 3000 micrograms or more per square centimeter of skin.

The composition should be topically applied to a selected area of the body from which it is desired to inhibit hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency of hair removal (shaving, tweezing, depilatory use, waxing) is reduced, or the subject perceives less hair on the treated site, or quantitatively, when the weight of hair removed by shaving (i.e., hair mass) is reduced. Benefits of reduced hair removal frequency include convenience and less skin irritation.

Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a particular PKC inhibitor, the flank organs of each of a group of hamsters are depilated by applying a thioglycolate based chemical depilatory (Surgex). To one organ of each animal 10–25 μl. of vehicle alone once a day is applied, while to the other organ of each animal an equal amount of vehicle containing a PKC inhibitor is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide an inhibition in hair growth of at least about 35%, more preferably at least about 50%, and most preferably at least about 70% when tested in the Golden Syrian hamster assay.

A number of PKC inhibitors were tested in the Golden Syrian hamster assay; the results are presented in Table 1.

TABLE I

| Compound | Vehicle[a] | Dose | pH | Hair Mass (mean ± SEM) | | % Inhibition |
|---|---|---|---|---|---|---|
| | | | | Untreated | Treated | |
| Verapamil | A | 10% | 5.5 | 1.45 ± .12 | 0.43 ± .05 | 69 ± 5 |
| Thioridazine | A | 10% | 4.5 | 2.41 ± .19 | 0.74 ± .07 | 68 ± 4 |
| Curcumin | C | 10% | 5.5 | 1.66 ± .19 | 0.55 ± .11 | 68 ± 5 |
| Trifluoperizine | A | 10% | 7.5 | 2.38 ± .25 | 1.03 ± .16 | 56 ± 6 |
| H-7[b] | A | 10% | 6.0 | 1.76 ± .18 | 0.81 ± .08 | 54 ± 3 |
| L-Ascorbic acid 6-palmitate | A | 10% | 8.5 | 2.82 ± .31 | 1.48 ± .14 | 46 ± 5 |
| Glycyrrhetinic acid glycoside | A | 10% | 4.0 | 1.84 ± .19 | 0.94 ± .17 | 46 ± 10 |
| 18β-Glycyrrhetinic acid | B | 7.5% | 7.5 | 2.01 ± .22 | 1.07 ± .10 | 44 ± 6 |
| Imipramine | A | 10% | 5.5 | 1.52 ± .22 | 0.94 ± .18 | 38 ± 5 |
| Phentolamine | A | 10% | 6.0 | 2.05 ± .27 | 1.61 ± .22 | 19 ± 9 |

[a]Vehicle A includes pure water (68%), ethanol (16%), propylene glycol (5%), dipropylene glycol (5%), benzyl alcohol (4%) and propylene carbonate (2%); vehicle B includes ethanol (80%), pure water (10%) and dipropylene glycol (10%); and vehicle C includes acetone (40%), ethanol (20%), DMSO (20%), and water (20%)
[b]H-7 is 1-(5-isoquinolinylsulfonyl)-2-methylpiperazine.

PKC activity was assayed in hair follicles isolated from flank organs using a commercial assay kit obtained from GIBCO BRL (Gaithersburg, Md.). The assay is based on the phosphorylation (incorporation of $^{32}$-P into) of acetylated-myelin basic protein. After isolation, the flank organ hair follicles were washed in phosphate-buffered saline and homogenized in a buffer containing 20 mM Tris, pH 7.5, 0.5 mM EDTA, 0.5% Triton X-100, 10 mM β-mercaptoethanol, and 25 μg/each of the protease inhibitors aprotinin and leupeptin. The hair follicle homogenate was added to the PKC reaction mixture at a final concentration of 10–20 μg/assay. The assay also included buffer, H$_2$O, phospholipid. The assay was performed in the presence or absence of select PKC inhibitors. The reaction mixture volume was 50 μl, the $^{32}$P-ATP substrate was added in a volume of 10 μl. The reaction proceeded at 32° for 15 minutes, whereupon a 16.3 μL aliquot was removed from the reaction mixture and spotted onto a paper filter. Filters were washed twice in 1% phosphoric acid with gentle shaking for 5 minutes. Filters were then washed twice in H$_2$O and placed in scintillation vials. $^{32}$P-Incorporation, a measure of the enzyme activity, was determined using standard liquid scintillation techniques. A significant inhibition was observed with thioridazine (30% inhibition at 500 μM) and trifluoperizine (42% inhibition at 500 μM)—which are thought to interfere with the phospholipid binding site—as well as with H-7, the most selective of PKC inhibitors and ATP binding site antagonist. An 86% inhibition of phosphorylation due to inhibition of PKC activity was produced by 200 μM H-7. Inhibition of PKC activity was nearly 100% with glycyrrhetinic acid glycoside (glycyrrhizine) at 200 μM; and 52% with 18β-glycyrrhetinic acid at 500 μM.

It will be appreciated by those skilled in the art that the invention can be performed within a wide range of equivalent parameters of composition and conditions without departing from the spirit or scope of the invention or of any embodiment thereof.

We claim:

1. A process for inhibiting mammalian hair growth, comprising
   selecting an area of skin from which reduced hair growth is desired; and
   applying to said area of skin a composition of an inhibitor of protein kinase C in an amount effective to reduce hair growth.

2. The process of claim 1, wherein said inhibitor is verapamil.

3. The process of claim 1, wherein said inhibitor is thioridazine.

4. The process of claim 1, wherein said inhibitor is curcumin.

5. The process of claim 1, wherein said inhibitor is trifluoperizine.

6. The process of claim 1, wherein said inhibitor is 1-(5-isoquinolinylsulfonyl)-2-methylpiperazine.

7. The process of claim 1, wherein said inhibitor is L-ascorbic acid 6-palmitate.

8. The process of claim 1, wherein said inhibitor is glycyrrhetinic acid glycoside.

9. The process of claim 1, wherein said inhibitor is 18β-glycyrrhetinic acid.

10. The process of claim 1, wherein said inhibitor is imipramine.

11. The process of claim 1, wherein said inhibitor is phentolamine.

12. The process of claim 1, wherein said inhibitor is an isoquinoline sulfonamide.

13. The process of claim 1, wherein said inhibitor is a bisindolylmaleimide.

14. The process of claim 1, wherein said inhibitor is a phenothiazine.

15. The process of claim 1, wherein said inhibitor is a lysosphingolipid.

16. The process of claim 1, wherein said inhibitor is a staurosporine.

17. The process of claim 1, wherein said inhibitor is selected from the group consisting of polymyxin B, sangvamycin, and doxorubicin-Fe(III).

18. The process of claim 1, wherein said inhibitor is balanol.

19. The process of claim 1, wherein said inhibitor is a substituted indolocarbazole.

20. The process of claim 1, wherein said inhibitor is a 2-(aminomethyl)piperidine.

21. The process of claim 1, wherein said inhibitor is 4-propyl-5(4-pyridinyl)-2-(3H)-oxazolone.

22. The process of claim 1, wherein said inhibitor is dequalinium.

23. The process of claim 1, said area of skin including hair follicles including PKC, wherein said inhibitor interacts with the ATP binding site in said PKC to inhibit the activity of said PKC to cause said reduction in hair growth.

24. The process of claim 1, said area of skin including hair follicles including PKC, wherein said inhibitor interacts with the calcium binding cite in said PKC to inhibit the activity of said PKC to cause said reduction in hair growth.

25. The process of claim 1, said area of skin including hair follicles including PKC, wherein said inhibitor interacts with the region in said PKC which interacts with phospholipid to cause said reduction in hair growth.

26. The process of claim 1, wherein said inhibitor is an irreversible inhibitor.

27. The process of claim 1, wherein the concentration of said inhibitor in said composition is between 1% and 30%.

28. The process of claim 1, wherein the composition is applied to the skin in an amount of from 100 to 3000 micrograms of said inhibitor per square centimeter of skin.

29. The process of claim 1, wherein the composition is applied to the skin on the face of said mammal.

30. The process of claim 1, wherein the composition provides a reduction in hair growth of at least 30% when tested in the Golden Syrian hamster assay.

31. The process of claim 1, wherein the composition provides a reduction in hair growth of at least 50% when tested in the Golden Syrian hamster assay.

32. The process of claim 1, wherein the composition provides a reduction in hair growth of at least 70% when tested in the Golden Syrian hamster assay.

33. The process of claim 1, wherein said mammal is a human.

* * * * *

UNITED STATES PATENT AND TRADEMARK OFFICE
CERTIFICATE OF CORRECTION

PATENT NO.  : 5,554,608

DATED       : September 10, 1996

INVENTOR(S) : Gurpreet S. Ahluwalia, Douglas Shander and Peter Styczynski

It is certified that error appears in the above-identified patent and that said Letters Patent is hereby corrected as shown below:

In col. 3, line 13, Table I, after 18$\beta$-Glycyrrhetinic acid, third column, move "7.5%" to directly underneath the column.

In col. 3, line 20, Table I, starting with "$^b$H-7", place an extra carriage return between that line and the previous line.

Signed and Sealed this

Ninth Day of December, 1997

Attest:

BRUCE LEHMAN

Attesting Officer

Commissioner of Patents and Trademarks